United States Patent [19]

Suddick et al.

[11] 4,217,341
[45] Aug. 12, 1980

[54] COMPOSITION AND METHOD FOR INHIBITING THE ADHERENCE OF DENTAL PLAQUE-PRODUCING BACTERIA TO SMOOTH SURFACES

[75] Inventors: Richard P. Suddick; Robert H. Staat; Ronald J. Doyle, all of Louisville, Ky.

[73] Assignee: The University of Louisville, Louisville, Ky.

[21] Appl. No.: 858,182

[22] Filed: Dec. 7, 1977

[51] Int. Cl.$^2$ .................. A61K 9/68; A61K 7/16; A61K 7/26; A61K 35/78
[52] U.S. Cl. .................. 424/48; 424/49; 424/58; 424/195
[58] Field of Search .................. 424/48–58, 424/195

[56] References Cited

U.S. PATENT DOCUMENTS

| 3,317,386 | 5/1967 | Humble | 424/195 |
| 3,952,092 | 4/1976 | Bowen et al. | 424/50 |

OTHER PUBLICATIONS

Kashket et al., Archs. Oral Biol. vol. 20: 375–379 (1975) "Aggregation of Oral Streptococci in the Presence of Concanavalin A".
J. D. R. 55(B) Feb. 1976 B268–B269; Abstract Papers #827, #828, #829 "Plaque Inhibition by Plant Cell Wall Fractions".
J. D. R. 56(B) Jun. 1977 B120–B218; Abstract Papers #273, #665 "Plaque Inhibition by Plant Cell Wall Fractions".
Liener J. Agr. Food Chem. 22: 17–22. (1974); Phytohemagglutinins: Their Nutritional Significance.
Lis et al.; Ann. Rev. Biochem. 42: 541–574; (1973) The Biochemistry of Plant Lectins (Phytohemagglutinins).
Jaffe, W. G. (1969), Hemagglutinins Toxic Constituents of Plant Foodstuffs; Edited by Liener i.e., pp. 69–101, Academic Press, N.Y., N.Y.

Primary Examiner—Shep K. Rose
Attorney, Agent, or Firm—Luedeka & Hodges

[57] ABSTRACT

A composition and method for inhibiting the adherence of dental plaque-producing bacteria to smooth surfaces including a lectin as an active ingredient thereof.

19 Claims, No Drawings

COMPOSITION AND METHOD FOR INHIBITING THE ADHERENCE OF DENTAL PLAQUE-PRODUCING BACTERIA TO SMOOTH SURFACES

This invention relates to compositions and methods for inhibiting the adherence of dental plaque-producing bacteria to smooth surfaces and particularly to a composition and method of this type containing one or more lectins.

Dental caries is generally believed to be caused by streptococcal species of bacteria, specifically, *Streptococcus mutans* (*S. mutans*), which appear to be able to attach to the tooth surface. It is also generally accepted in the field of oral biology that dental caries results when the tooth surface underlying a gelatinous bacterial colony, termed "dental plaque" or "plaque," becomes decalcified as a result of the acidogenic potential of the entire mass of bacteria in each specific plaque deposit. Dietary sucrose is generally believed to be the principal metabolite utilized by the acidogenic bacteria of plaque, causing acid production and subsequent decalcification. Specifically, heretofore it has been accepted that glucans produced from sucrose by the microbe's glucosyltransferases (GTF) have been indicated as the primary factor in adherence of the microbe to smooth surfaces. Further, it has been demonstrated that gingival inflammation, the first state of peridontal disease, is directly correlated with the total mass of dental plaque which accumulates on the tooth surfaces close to the gum line.

Lectins, also known as hemagglutinins, generally comprise a large number of crude or purified proteins or glycoproteins of plant or animal origin which have been characterized or identified by their ability to agglutinate suspensions of red blood cells derived from human blood or blood of other animals. It is this property which has spawned their collective designation as hemagglutinins.

It has been known heretofore that *Concanavalin A*, a lectin derived from the jack bean, will agglutinate *S. mutans*, but this lectin has been demonstrated to increase the adherence of *S. mutans* to smooth surfaces, such as hydroxyapatite, similar or equivalent to smooth surfaces in the nature of tooth enamel. To the contrary, the present inventors have found that specific lectins will bind and agglutinate suspensions of *S. mutans* and similar dental decay-causing bacteria, and further have found that these lectins inhibit the adherence of these bacteria to smooth surfaces such as the surfaces equivalent to tooth enamel. Thus, the present invention is directed to the prevention of the initial colonization of plaque-producing bacteria, such as on tooth surfaces, by agglutinating such bacteria before colonization occurs, and/or by inhibiting the adherence of such bacteria to the teeth.

It is therefore an object of this invention to provide a composition for inhibiting the adherence of dental plaque-producing bacteria to smooth surfaces. It is another object of this invention to provide a composition which agglutinates plaque-producing bacteria and which, simultaneously, inhibits the adherence of such bacteria to smooth surfaces. It is another object to provide a toothpaste, mouthwash, chewing gum, or the like composition containing one or more lectins having the capability of inhibiting the adherence of plaque-producing bacteria to smooth surfaces. It is another object to provide a method for inhibiting the adherence of dental-plaque-producing bacterial to a smooth surface.

In accomplishing the objects of this invention, the inventors have found that certain lectins bind to and agglutinate bacteria, namely *S. mutans*, and similar bacteria, which are normally considered to be a cause of dental caries and/or peridontal disease and further inhibit the adherence of these bacteria to smooth surfaces. As described herein, lectin-induced agglutination and inhibited adherence of plaque-producing and/or cariogenic bacteria which are present in the mouth, suspended in saliva, or on the surfaces of the mucous membranes or gingivae, causes these bacteria to be cleared or removed from the mouth more readily by natural means, that is, the agglutinated masses whose ability to adhere to smooth surfaces has been substantially reduced, are more readily swept away and swallowed with the saliva which is being continually secreted as a basal rate into the oral cavity (individuals normally swallow 2-3 times per minute while awake). It has been found by the present inventors that these lectin containing compositions, when allowed to interact with plaque-producing and/or cariogenic bacteria, prevent these bacteria from being able to adhere to smooth surfaces such as the smooth enamel surfaces of the teeth. In this manner the bacteria are not able to adhere to the tooth surface and are not able to colonize the surface and form the dental plaque deposits which, as a by-product of their metabolism, produce acids which decalcify the tooth beneath the deposits, resulting in decay. It appears that the mechanism by means of which the lectins react with the bacteria is of the antigen-antibody type so that in addition to the agglutination and nonadherence characteristics produced by the lectin-containing composition the interaction appears to create numerous new lectin-bacterial antigen complexes in the mouth which in turn will be effectively neutralized and cleared from the oral cavity by natural salivary antibodies directed against this distinctive lectin-bacterial antigen, thereby further inhibiting the adherence of these bacteria to the teeth by virtue of the capability of the lectin-containing composition to induce the salivary secretory antibody response to the lectin-bacterial complex.

The lectins of the present invention are in part identified by their ability to agglutinate human red blood cells. It appears that only those lectins which will agglutinate red blood cells will agglutinate plaque-producing bacteria. Accordingly, this characteristic of a lectin is a measure of its suitability in a composition for inhibiting the adherence of the bacteria in question.

In accordance with the present disclosure, a lectin of the hereinafter specified type is combined with a carrier which may be a liquid, gel or gum base vehicle as are well known in the dentifrice art for use as a mouthwash, mouth rinse, toothpaste, or the like or incorporated into a chewing gum. In this manner, the effective ingredient of the composition, namely the lectin, is carried to the bacteria in the oral cavity whereupon the bacteria and lectin interact such that their ability to adhere to the tooth surface is inhibited so that the bacteria are flushed away either by the physical act of brushing, washing or rinsing, or they are swept away by the normal saliva flow.

As the active ingredient, there is chosen a lectin that exhibits an inhibition of the adherence of bacteria equivalent to the inhibition exhibited by the lectin derived from the seed of *Persea americana* (*P. americana*); *Ar-* chais hypogaea (A. hypogaea); Magiferia indica (M. indica); Cucurbita pepo (C. pepo); or Phaseolus vulgaris (P. vulgaris) to the adherence of Streptococcus mutans (S. mutans) when tested by the glass vial technique, which in no event is greater than a fifty (50%) percent adherence as defined by the equation:

$$\% \text{ adherence of bacteria} = \frac{3_H - CPM \text{ experimental assay}}{3_H - CPM \text{ control assay}} \times 100 \quad \text{(Eq. 1)}$$

In the adherence assay referred to above, the S. mutans 6715 is grown anaerobically overnight in brain heart infusion supplemented with a 2 μCi $3_H$-thymidine (20 Ci/mM/ml), following which the bacteria cells are recovered from the medium by centrifugation and washed three times in 0.05 M phosphate buffer, pH 6.6 (PB). The washed cells are resuspended to an optical density (A600, 1 cm) of 1.0 after the third wash in phosphate buffer containing 0.5 mg/ml. sodium fluoride and 20 mg/ml chloramphenicol. Typically, 10 μl of the $3_H$-labelled cell suspension gives $3\text{-}4 \times 10^3$ CPM.

For assaying, 0.9 ml of the cells are placed in scintillation vials (Vitro "180," 20 ml, No. 300-1A, Wheaton Scientific, Millville, N.J.) with 0.1 ml PB and 0.1 ml sucrose (8 mg/ml) to a final volume of 1.1 ml. After incubation at 37° C., the unattached bacteria are removed by tilting the vials and aspirating off the fluid from the lower side of each vial with a Pasteur pipette. Residual free bacteria are removed using three 2.0 ml. washes with PB. The PB is slowly added down the side of the vial, the vial is gently mixed by rotation on a flat surface, and the fluid is removed by aspiration as described above. The vials are dried for 15 minutes under a heat lamp, and the amount of radioactivity remaining is measured using the scintillation fluid and counting procedure described by B. Guggenhiem and E. Newbrun in their publication entitled "Extracellular glucosyltransferase activity of an HS strain of Streptococcus mutans" Helv. Odontal. Acta, Volume 13, pp. 84–97, 1969. The reproducibility of the adherence assay is determined by performing up to 20 duplicate trials.

Further adherence assays may be conducted to measure the inhibition of adherence of the S. mutans to hydroxyapatite by lectin-containing compositions using the radiolabeled microbe systems detailed by W. F. Liljemark and S. V. Schauer in Oral Biology, Volume 20, pp. 609–615 (1975).

Employing these assay techniques, lectins derived from P. americana, A. hypogaea, P. vulgaris, C. pepo, and M. indica when present in a solution having a concentration equivalent to a hemagglutination titer of 1:128 consistently produce a percent adherence of bacteria less than 50% of control adherence. That is to say that less than half of the bacteria attach themselves to the smooth surface of the glass vial. Of these lectins, P. americana consistently inhibits attachment of more than 90% of the bacteria, relative to the control value (The control of all cases being identical to the experimental material minus the lectin.)

Those lectins suitable as the active ingredient in the present composition are further categorized by their chemical specificities with respect to red blood cell or bacteria cell agglutination tests. "Specificity" for present purposes refers to the specific sugar, or amino sugar, protein or peptide which, if added to the present composition, will inhibit the ability of the lectin to interfere with adherence. Specifically, those lectins which display a chemical specificity to D-Galactose (D-Gal), (α-D-Galactos)$_2$. L-Fucose, N-Acetylneuraminic Acid (NANA), basic proteins, or peptides, and which exhibit a percent adherence of 50% or less produce the desired agglutination and adherence inhibition properties. In this category there are included the lectins listed in Table I.

TABLE I

| Lectin | % Adherence | Specificity |
|---|---|---|
| Arachis hypogaea | 20 | (α-D-Galactose)$_2$ |
| Persea americana | 11 | basic proteins |
| Mangiferia indica | 11 | ? |
| Cucurbita pepo | 43 | ? |
| Phaseoleus vulgaris | 38 | α-D-GalNAc |

On the other hand, those lectins which exhibit a chemical specificity to α-D-Galactose (α-D-Gal), α-D-Glucose (α-D-Gle), α-D-Manose (α-D-Man), N-Acetyl-D-Glucosamine (D-GLcNAc), or N-Acetyl-D-Glucosamine (D-GlcNAc) and which exhibit a percent adherence greater than 50% have been found unsuitable for the purposes of the composition disclosed herein. In this category there are included the lectins listed in Table II.

TABLE II

| Lectin | % Adherence | Specificity |
|---|---|---|
| Canavalia ensiformis | 115 | α-D-Glc |
| Triticum vulgaris | 99 | (D-GlcNAc)$_2$ |
| Bandeiraea simpliciforia | 91 | α-D-Gal |

The extract from P. americana (avocado) seeds is obtained by grinding the seed with phosphate buffer-saline, followed by removal of the insoluble material. The working concentration in adherence assays is defined as 1:128 hemagglutination titer. Assay are performed in round bottom microtiter plates with 50 ml 3% washed human red blood cells (type A) and 50 ml of extract. The concentration of extract is 1 mg/ml in PB-saline, pH 7.2. Following physical and chemical characterization of this extract, as referred to below, the extract is dialyzed against distilled-deionized H$_2$O and lyophilized.

The lectin-like activity of the P. americana extract exhibits the physical and chemical properties shown in TABLE III.

TABLE III

| Treatment | Red Blood Cell Titer |
|---|---|
| Control, dialyzed, freeze-dried | 512 |
| Autoclaving, 15 PSI, 15 minutes | 512 |
| Pronase (20 μg/ml), pH 7.2 :18 hr, 37° C. | 512 |
| Extraction with N-butanol, hexane, dioxane, acetone, chloroform-methanol (2:1 v/v) or ethanol | 512 |
| Dialysis vs 1% SDS | 512 |
| Dialysis vs 0.1 N HCl | 512 |
| Dialysis vs 50 mM EDTA, pH 5.3 | 512 |
| Dialysis vs 8M urea | 512 |
| Dialysis vs 0.1 N NaOH | 16 |

While the hemagglutination activity of the P. americana extract is quite stable to most physical or chemical treatments, the activity precipitates for solution during prolonged storage. The lectin appears to have an affinity for basic proteins and not carbohydrates. The hemagglutinating activity is not inhibited by either D-glucose, D-galactose, D-mannose, N-acetylglucosamine, N-acetylgalactosamine, D-glucosamine, D-galactosamine, D or L-fucose, D-arabinose, sucrose or lactose. The extract precipitates with trypsin, arginine-rich histones, lysine-rich histones, lysozyme, ribonuclease and polylysine. However, the extract will not precipitate with pepin, polyaspartic acid, polyglutamic acid or human a-acid glycoproteins. Thus, the lectin-like activity in *P. americana* extract is possibly a result of an interaction between basic groups on cell surfaces with oppositely charged lectin molecules.

The inventors have found that the *P. americana* lectin interacts with the surface of *S. mutans* 6715 and pretreatment of either glass surfaces or saliva-coated hydroxyapatite with lectin has relatively insignificant effects on the sucrose-dependent adherence.

TABLE IV

Effect of 30 minute pretreatment of either the absorbing surface [glass or saliva coated hydroxyapatite (SHA)] or *S. mutans* 6715 cells with *P. americana* lectin.

|  | % Adherence |
|---|---|
| Glass surfaces |  |
| no lectin | 100 |
| microbe pretreated | 1 |
| glass pretreated | 77 |
| SHA surface |  |
| no lectin | 100 |
| microbe pretreated | 10 |
| SHA pretreated | 59 |

Whereas *P. americana* lectin appears to interact with the bacteria, as opposed to the smooth surface, it is possible that other lectins may be effective through the mechanism of an interaction with the smooth surface.

The adherence inhibition of *S. mutans* 6715 by the *P. americana* lectin is concentration dependent (See TABLE V). In addition, exposure of the lectin to fresh washed human RBC (Type A) removes the *S. mutans* adherence inhibitory properties from the extract.

TABLE V

Effect of dilution of the *P. americana* lectin on sucrose-dependent adherence of *S. mutans* 6715. The undiluted (1:1) lectin's hemagglutination titer is 1:128. Note that the adherence assay titers are not adjusted for the 1:11 dilution inherent in the assay.

| Extract: Total Volume | % Adherence |
|---|---|
| 1:1 | 3 |
| 1:2 | 7 |
| 1:4 | 17 |
| 1:8 | 49 |
| 1:16 | 69 |
| 1:32 | 94 |
| 1:128 | 98 |

The ability of the *P. americana* lectin to alter the sucrose-dependent glucan synthesis by *S. mutans* GTF, as shown in TABLE V, indicates that the rate of total glucan synthesis is not altered by the lectin. In addition, there was found no significant lectin-induced difference in the amount of water-soluble polysaccharide.

The lack of effect by the *P. americana* lectin on polysaccharide synthesis is a rather unexpected result. Through additional work, the inventors have found that the lectin-hemagglutination activity could not be removed by exposure to high concentrations of commercial dextrans, pseudonigeran ($\alpha$-1, 3-glucan) or *S. mutans* 6715 glucan. Thus, it was found that none of the glucose-containing compounds shown in TABLE VI moderated the lectin's adherence-inhibition activity.

TABLE VI

Effect of 30 minute preincubation of the *P. americana* lectin with glucose-containing compounds (final concentration of 1 mg/ml) on the sucrose-dependent adherence of *S. mutans* 6715. Control adherence=100%.

| *P. americana* pretreatment | % Adherence |
|---|---|
| none | 5 |
| glucose | 4 |
| isomaltose | 4 |
| Dextran T 10 | 5 |
| Dextran T 500 | 6 |
| *S. mutans* glucan | 6 |

In addition to the *S. mutans* 6715, the present composition has been found to be substantially equally effective in agglutinating and inhibiting the adherence of other *S. mutan* strains or isolates, namely, E-49, 10449, LM-7, KIR, B$_2$, and FA-1, plus *S. sanguis* and *S. mitis*.

In one embodiment of the present composition, the lectin in its natural state is incorporated into a vehicle, such as a buffer solution, until it is introduced into the oral cavity, thereby maintaining the lectin in its active state until combined with natural oral fluids and saliva through a tooth brushing activity, or through the rinsing of the mouth, or through the chewing of a gum that contains the lectin.

In accordance with the method of the invention, bacteria of the dental-plaque-producing type are contacted by a solution containing lectin selected in accordance with the criteria set forth herein. In a preferred method, the lectin is in solution with a liquid that is inert with respect to the lectin such as a phosphate buffer as described hereinbefore.

In the present disclosure, specific lectins are described to provide a standard for the selection of a lectin by a person skilled in the art as being suitable for use in the present composition. It is to be recognized that such persons can select other lectins having like properties and/or characteristics as disclosed herein to provide the desired inhibition of the adherence of plaque-producing bacteria and there is no intention to limit the invention except as set forth in the appended claims.

What is claimed:

1. A composition for inhibiting the adherence of dental-plaque producing bacteria to a smooth surface including a carrier material and an effective quantity of a lectin, said lectin being of the type exemplified by the extract obtained by grinding the seed of a plant chosen from a group comprising *Arachis hypogaea, Persea americana, Mangiferia indicia, Cucurbito pepo,* or *Phaseolus vulgaris* in a phosphate-saline buffer solution, said lectin being present in a concentration equivalent to a hemagglutination titer of 1:128, whereby said lectin reduces the adherence of said bacteria to a value less than 50 percent as tested by the glass vial technique.

2. The composition of claim 1 wherein said lectin exhibits a chemical specificity with respect to a red blood cell or bacteria agglutination test to d-Galactose, ($\alpha$-D-Galactose)$_2$, L-Fucose, N-Acetylneuraminic Acid, basic peptides, or basic proteins.

3. The composition of claim 1 wherein said lectin exhibits the chemical specificities with respect to a red blood cell or bacteria agglutination test as does the lectin derived from the seed of either *Arachis hypogaea, Persia, americana, Mangiferia indica, Cucurbito pepo,* or *Phaseolus vulgaris.*

4. The composition of claim 1 wherein said lectin is derived from the seed of a plant chosen from the group comprising *Arachis hypogaea, Persea, americana, Mangiferia indica, Cucurbito pepo,* or *Phaseolus vulgaris.*

5. A dentifrice comprising a carrier material and an effective quantity of a lectin of the type exemplified by the extract obtained by grinding the seed of a plant chosen from the group comprising *Arachis hypogaes, Persea americana, Mangiferia indicia, Cucurbito pepo,* or *Phaseolus vulgaris* in a phosphate-saline buffer solution, said lectin being present in a concentration equivalent to a hemagglutination titer of 1:128, whereby said lectin reduces the adherence of bacteria of the dental-plaque-producing type to a value of less than 50 percent as tested by the glass vial technique.

6. The dentifrice of claim 5 wherein said lectin exhibits a chemical specificity with respect to a red blood cell or bacteria agglutination test to D-Galactose, (α-D-Galactose)₂, L-Fucose, N-Acetylneuraminic Acid, basic peptides, or basic proteins.

7. The dentifirce of claim 5 wherein said lectin exhibits the chemical specificities with respect to red blood cell or bacteria agglutination tests as does the lectin derived from the seed of either *Arachis hypogaea, Persea americana, Mangiferia indica, Cucurbito pepo,* or *Phaseolus vulgaris.*

8. The dentifrice of claim 5 wherein said lectin is derived from the seed of a plant chosen from the group comprising *Arachis hypogaea, Persea americana, Mangiferia indica, Cucurbito pepo,* or Phaseolus vulgaris.

9. A mouthwash for inhibiting the adherence of dental-plaque producing bacteria to a smooth surface including a liquid carrier material and an effective quantity of a lectin of the type exemplified by the extract obtained by grinding the seed of a plant chosen from the group comprising *Arachis hypogaea, Persea americana, Mangiferia indicia, Cucurbito pepo,* or *Phaseolus vulgaris* in a phosphate-saline buffer solution, said lectin being present in a concentration equivalent to a hemagglutination titer of 1:128, whereby said lectin reduces the adherence of dental plaque-producing bacteria to a value less than 50 percent as tested by the glass vial technique.

10. The mouthwash of claim 9 wherein said lectin exhibits a chemical specificity with respect to a red blood cell or bacteria agglutination test to D-Galactose, (α-D-Galactose)₂, L-Fucose, N-Acetylneuraminic acid, basic peptides, or basic proteins.

11. The mouthwash of claim 9 wherein said lectin exhibits the chemical specificities with respect to a red blood cell or bacteria agglutination test as does the lectin derived from the seed of either *Arachis hypogaea, Persea, americana, Mangiferia, indicia, Cucurbito pepo,* or *Phaseolus vulgaris.*

12. The mouthwash of claim 9 wherein said lectin is derived from the seed of a plant chosen from the group comprising *Archais hypogaea, Persea americana, Mangiferia indica, Cucurbito pepo,* or *Phaseolus vulgaris.*

13. A chewing gum for inhibiting the adherence of dental-plaque producing bacteria to a smooth surface including a carrier material and an effective quantity of a lectin, said lectin being of the type exemplified by the extract obtained by grinding the seed of a plant chosen from the group comprising *Arachis hypogaea, Persea americana, Mangiferia indicia, Cucurbito pepo,* or *Phaseolus vulgaris* in a phosphate-saline buffer solution, said lectin being present in a concentration equivalent to a hemagglutination titer of 1:128, whereby said lectin reduces the adherence of said bacteria to a value less than 50 percent as tested by the glass vial technique.

14. The chewing gum of claim 13 wherein said lectin exhibits a chemical specificity with respect to a red blood cell or bacteria agglutination test to D-Galactose, (α-D-Galactose)₂, L-Fucose, N-Acetylneuraminic Acid, basic peptides, or basic proteins.

15. The chewing gum of claim 13 wherein said lectin exhibits the chemical specificities with respect to a red blood cell or bacteria agglutination test as does the lectin derived from the seed of either *Arachis hypogaea, Persia americana, Mangiferia indica, Cucurbito pepo,* or Phaseolus vulgaris.

16. The composition of claim 13 wherein said lectin is derived from the seed of a plant chosen from the group comprising *Arachis hypogaea, Persea americana, Mangiferia indica, Cucurbito pepo,* or Phaseolus vulgaris.

17. A composition for inhibiting the adherence to a smooth surface of bacteria of the dental-plaque-producing type comprising an effective quantity of a lectin derived from the seed of *Persea americana.*

18. A method for inhibiting the adherence of bacteria of the dental-plaque-producing type to a smooth surface comprising the step of subjecting said bacteria to a composition containing an effective quantity of a lectin of the type exemplified by the extract obtained by grinding the seed of a plant chosen from the group comprising *Arachis hypogaea, Persea americana, Mangiferia indicia, Cucurbito pepo* or Phaseolus vulgaris in a phosphate-saline buffer solution, said lectin being present in a concentration equivalent to a hemagglutination titer of 1:128, whereby said lectin reduces the adherence of said bacteria to a value less than 50 percent as tested by the glass vial technique.

19. The method of claim 18 wherein the ratio of lectin extract volume to the total volume of extract and bacteria solution is equal to or less than about 1:8.

* * * * *